(12) United States Patent
Vilsmeier

(10) Patent No.: US 11,978,561 B2
(45) Date of Patent: *May 7, 2024

(54) DETERMINING AN INDICATOR RELATING TO INJURY

(71) Applicant: Brainlab AG, Munich (DE)

(72) Inventor: Stefan Vilsmeier, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/103,379

(22) Filed: Jan. 30, 2023

(65) Prior Publication Data

US 2023/0253111 A1    Aug. 10, 2023

Related U.S. Application Data

(63) Continuation of application No. 16/340,273, filed as application No. PCT/EP2016/081221 on Dec. 15, 2016, now Pat. No. 11,568,989.

(51) Int. Cl.
*G16H 50/20*    (2018.01)
*A61B 5/02*    (2006.01)
(Continued)

(52) U.S. Cl.
CPC ............... *G16H 50/20* (2018.01); *A61B 5/02* (2013.01); *G06N 3/08* (2013.01); *G06N 20/00* (2019.01); *A61B 2562/0219* (2013.01)

(58) Field of Classification Search
CPC .......... G16H 50/20; G16H 50/70; A61B 5/02; A61B 2562/0219; G06N 3/08; G06N 20/00

(Continued)

(56) References Cited

U.S. PATENT DOCUMENTS

2014/0052405 A1* 2/2014 Wackym ............... A61B 5/6803
                                                                     702/141
2014/0095206 A1* 4/2014 Fung ..................... G16H 50/30
                                                                     705/3

(Continued)

OTHER PUBLICATIONS

International Search Report and Written Opinion issued in PCT Application No. PCT/EP2016/081221 dated Oct. 4, 2017.

*Primary Examiner* — Omar Casillashernandez
(74) *Attorney, Agent, or Firm* — Gray Ice Higdon

(57) ABSTRACT

Disclosed is a medical data processing method for determining an indicator relating to an injury of an anatomical structure (1) of a patient, wherein the method comprises executing, on at least one processor (5) of at least one computer (3), steps of:
a) acquiring (S1) acceleration data describing an energy of a set of one or more signals in dependence on both time and frequency, the set of signals acquired by measuring the acceleration of the anatomical structure (1) over time;
b) acquiring (S2) analysis data describing an analysis rule for determining at least one of
b1) an overall energy level of at least one signal of the set of signals,
b2) a correlation between at least two signals of the set of signals in the frequency domain, the at least two signals respectively measured at at least two different respective regions of the anatomical structure (1), or
b3) a relationship between energies given for at least two different frequency ranges of at least one signal of the set of signals;
c) determining (S3) indicator data describing the indicator based on the acceleration data and the analysis data.

10 Claims, 5 Drawing Sheets

(51) Int. Cl.
*G06N 3/08* (2023.01)
*G06N 20/00* (2019.01)

(58) Field of Classification Search
USPC .......................................................... 706/12
See application file for complete search history.

(56) References Cited

U.S. PATENT DOCUMENTS

| | | | |
|---|---|---|---|
| 2014/0275960 A1* | 9/2014 | Hubbard | G01R 33/4806 600/410 |
| 2015/0196252 A1* | 7/2015 | Iuliano | A61B 5/746 600/595 |
| 2016/0296153 A1* | 10/2016 | Lovoi | A61B 7/04 |
| 2018/0028091 A1* | 2/2018 | Huang | A61B 5/1123 |
| 2021/0295668 A1* | 9/2021 | Blanchard | G06N 3/042 |

* cited by examiner

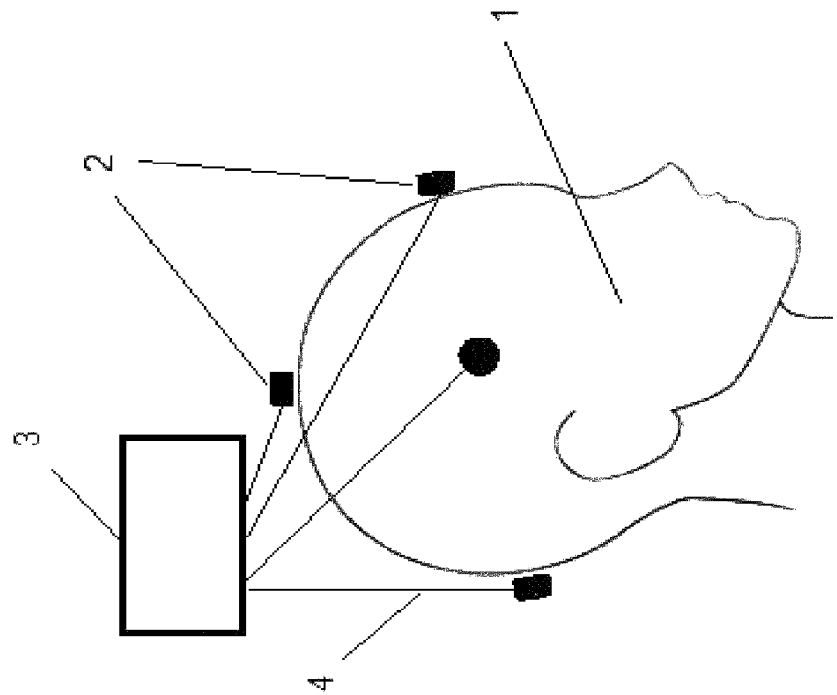
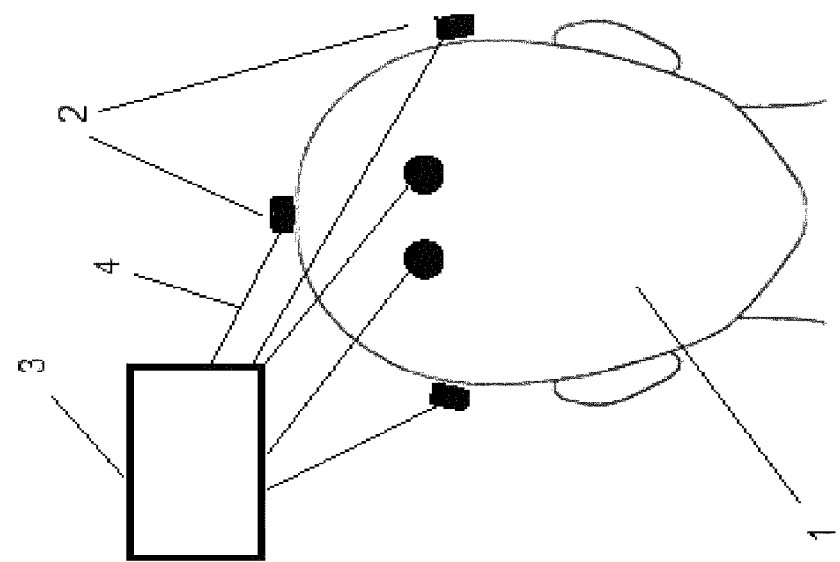
Fig. 1a
Fig. 1b

DETERMINING AN INDICATOR RELATING TO INJURY

The present invention relates to a medical data processing method for determining an indicator relating to an injury of an anatomical structure of a patient, a corresponding computer program, a non-transitory program storage medium storing such a program and a computer for executing the program, as well as a system configured to determine an indicator relating to an injury of an anatomical structure of a patient.

TECHNICAL BACKGROUND

Using acceleration sensors for detecting physical properties of a patient is known in the state of the art. For example, WO 2016/173626 A1 describes a detection of the heartbeat in cranial accelerometer data using independent component analysis.

The present invention allows for analyzing acceleration data to gain information with regard to an injury, for example a concussion, of a patient.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses determining acceleration data by means of at least one acceleration sensor attached to a patient's head. At least one time dependent acceleration signal is analyzed with respect to time and frequency, for example by means of a joint time frequency analysis (JFTA), in particular by applying a Fourier transformation to the acceleration signal for a plurality of time intervals. By considering an overall energy level of the at least one signal, a correlation between at least two signals measured by two sensors, a relationship between energies given for different frequency ranges of the at least one signal or a combination of these parameters an indicator for determining an injury, for example a concussion, is determined.

General Description of the Present Invention

In this section, a description of the general features of the present invention is given for example by referring to possible embodiments of the invention.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The disclosed method provides, in a first aspect, a medical data processing method for determining an indicator relating to an injury (for example, a potential injury) of an anatomical structure of a patient. The indicator may give an indication whether an injury is present or not. In one example, the indicator may be used as an indicator for assessing a probability of an injury. The indicator may be represented by a (for example, continuous) score which may be used to assess the probability of an injury. The indicator does not represent a diagnosis, however may be used by a medical doctor as a basis for a diagnosis.

In one example, the injury may be a concussion, swelling, fracture or rupture of the anatomical structure. The injury may be internal bleeding. The anatomical structure may be the head of a patient, in particular the brain. In one example, the injury may be a concussion of the brain.

The method comprises executing, on at least one processor of at least one computer, the following exemplary steps.

In a (for example first) exemplary step, acceleration data is acquired. The acceleration data describes an energy of a set of one or more signals in dependence on both time and frequency, the set of signals acquired by measuring the acceleration of the anatomical structure over time. In one example, for each of the set of one or more signals, the energy is respectively described (by the acceleration data) in dependence on both time and frequency. In one example, the energy of a signal may be a function of the amplitude of the signal. In one example, the energy may be represented by a non-signed (for example, absolute) value of the amplitude of the signal or by a square of the amplitude of the signal.

The set of one or more signals may have or had been acquired by measuring the acceleration of the anatomical structure. In other words, measuring may be performed during the (for example first) exemplary step. In one example, measuring the acceleration data may have been performed before the (for example first) exemplary step.

The acceleration data may be acquired by means of at least one (acceleration) sensor (for example, at least one gyro sensor), which has a fixed relative position with respect to the anatomical structure, for example is attached to the anatomical structure in order to detect an acceleration performed by the anatomical structure. The at least one acceleration sensor may be mounted to a head set. When the head set is arranged on a patient's head, the at least one acceleration sensor may be in (tight) contact with a region of the surface of the patient's head, for example the skin or the hair in order to detect an acceleration of the region. In one example, the acceleration data may be acquired by means of a measuring beam (for example, a laser beam) being directed to a region of a surface of the anatomical structure and the reflection of which being detected by a sensor in order to detect a movement over time and thus an acceleration of the region (by means of a laser distance measurement technique).

The acceleration data may be acquired by means of a plurality of (acceleration) sensors, for example two or more, in particular 6 or more (acceleration) sensors. In one example, the acceleration data is acquired by at least two sensors respectively arranged at different regions of the anatomical structure or respectively receiving signals from different regions of the anatomical structure.

In one example, the at least one acceleration sensor may record mechanical responses of the brain (for example vibrations from the brain), which are triggered, for example by the heartbeat of the patient and propagate through the brain matter. Accordingly, the heartbeat may function as a test beat for analyzing mechanical response properties, for example the resonance behavior of at least part of the brain. The response properties (for example resonance behavior) of at least part of the brain may be direction-dependent. Furthermore, the resonance behavior may be influenced by an injury, for example a concussion of the brain.

In one embodiment, the signals of a plurality of acceleration sensors are recorded simultaneously for a certain amount of time (for example, longer than 10 s or longer than 30 s or longer than 1 minute or longer than 2 minutes; for example shorter than 20 min or shorter than 10 minute or shorter than 5 minute). In one example the signals are recorded for 3 minutes. The outcome of recording may be a time-dependent electrical voltage signal (one per acceleration sensor), which may be digitized and stored. Accordingly, the at least one signal (for example, measured by the at least one acceleration sensor) may be a time-dependent electric voltage signal. The voltage represents for example the amplitude of acceleration or a function of the amplitude of acceleration (like an unsigned function, like absolute value or square of amplitude of acceleration). The energy of the signal is for example a function of the measured voltage (e.g. function of identity or unsigned function thereof like absolute value or square of voltage). The acceleration data acquired by each sensor may be normalized. The normalization may be performed by means of calibration of the sensors by performing the measurement on a (e.g. standardized) mechanical model of an anatomical structure (e.g.) brain which is mechanically excited to simulate influence of vital mechanical processes, like heart beat and/or breathing. Alternatively or additionally, the normalization may be performed by calculating an average of one or more energies (for example all energies or energies of a part of the spectrum) of the set of signals and dividing each signal by the average. In as far in the following the term "energy" is used, this may refer to a normalized or non-normalized energy.

In one example, the signal is acquired by analyzing a time dependent acceleration signal with respect to time and frequency, for example by means of a joint time frequency analysis (JFTA), for example by applying a (short-time) Fourier transformation (STFT) to the acceleration signal for a plurality of time intervals, for example a moving time window Fourier Transform (each time interval being for example longer than 10 ms or longer than 100 ms or longer than 1 s; for example shorter than 1 min or shorter than 10 s or shorter than 1 s)). The time-dependent signal of each sensor may be converted to the frequency domain, for example by means of a Fast Fourier Transform (FFT) where the time intervals are distinct or overlapping. Alternatively to STFT, for example, a continuous wavelet transform or other linear, quadratic or bilinear transforms may be used. Accordingly, a frequency spectrum of the energy may be acquired for the signal of each sensor as a function of time over the recording period. The frequency spectrum may depicted in a waterfall diagram. The frequency spectrum shows the energy as a function of time and frequency in two dimensions. In one example, the time range is from 0 to 60 s and the frequency range from 0 to 50 Hz.

In a (for example second) exemplary step, analysis data is acquired. The analysis data describes an analysis rule for determining (from the acceleration data) at least one of:

b1) an overall energy level of at least one signal of the set of signals, b2) a correlation between at least two signals of the set of signals in the frequency domain, the at least two signals respectively measured at at least two different respective regions of the anatomical structure, or b3) a relationship between energies given for at least two different frequency ranges of at least one signal of the set of signals.

In a (for example third) exemplary step, indicator data is determined. The indicator data describes the indicator based on the acceleration data and the analysis data. In one example, the indicator may be a binary indicator indicating the presence or non-presence of an injury. In one example the indicator may be used as an indication for a probability for the presence or non-presence of an injury, for example a concussion. In one example, the indicator may represent a score (for example, a continuous score) which can be used as an indicator for indicating a probability for the presence or non-presence of an injury, for example a concussion.

The overall energy level may present one parameter (for example, parameter1) for determining the indicator. A value for the overall energy level can be determined for one or more sensors (signals). For determining the overall energy level of at least one signal (generated by at least one sensor) of the set of signals from the acceleration data the method may, for example, comprise executing, on the at least one processor of the at least one computer, the step of acquiring threshold data describing a threshold for the energy (for example an energy threshold), wherein the overall energy level may be determined by comparing the threshold with the energy (for example normalized energy). With this regard, the energies (for example, in the frequency spectrum) below or above the threshold may be determined. The overall energy level is in particular determined by determining the portion of the energy which is above (an upper) threshold. Alternatively or additionally, the overall energy level is in particular determined by determining the portion of the energy which is below (a lower) threshold. The frequency range for which the portion is determined starts for example at 0 Hz or 1 Hz or 5 Hz and/or ends before 100 Hz or 50 Hz or 30 Hz. In one example, the frequency range starts at 0 Hz and ends at 30 Hz.

In one embodiment, for determining the above mentioned portions, the number of bins in a waterfall diagram depicting a frequency spectrum which have an energy above the threshold may be determined and a ratio between the number of bins above the threshold and the total number of bins is determined. The determined ratio represents an example for an overall energy level. If the (for example, total) number of bins is fixed, the number of bins above the threshold could be used as a value for the overall energy level. In one example, the portion of bins with a high energy (for example an energy above a specific threshold) represents an example for an overall energy level.

In one example, the threshold for the energy may be determined by means of a machine learning algorithm, as described below, for optimizing the parameter (for example, parameter1). In one example, the probability of an injury (for example, a concussion) may be assumed to be increased if the portion of energy which is above a threshold is larger than 80%.

The correlation between at least two signals of the set of signals in the frequency domain (or a sub-range thereof), the at least two signals respectively measured at at least two different respective regions of the anatomical structure, may present a further parameter (for example parameter2) for determining the indicator. In one example, the correlation is determined between signals of at least one pair of (acceleration) sensors (for example, all pairs of sensors) of a plurality of sensors. In one example, the correlation is determined by computing a correlation coefficient (in the frequency domain) describing a correlation between a first signal of the set of signals acquired at a first region of the anatomical structure and a second signal of the set of signals acquired at a second region of the anatomical structure. The first region and the second region may be different locations, positions or surface areas of the anatomical structure. In one embodiment, the first signal may be acquired by a first (acceleration) sensor. The second signal may be acquired by a second (acceleration) sensor. The first sensor and the second sensor may be selected out of a plurality of sensors used for acquiring the acceleration data by means of a machine learning algorithm, as described below, for optimizing the parameter (for example, parameter2). In one example, a correlation between the signals acquired by at least one pair of sensors (for example, all pairs of sensors) is determined and provided to the machine learning algorithm.

The correlation coefficient may be a Pearson correlation coefficient. In one example, the correlation coefficient is computed for a specific frequency range of two signals measured at two different regions of the anatomical structure, for example by the first (acceleration) sensor and the second (acceleration) sensor. The correlation of two signals measured by two sensors attached at different regions of the anatomical structure may provide information for determining the indicator. The regions are for example at opposing sides of the anatomical structure. The frequency range for which the correlation coefficient is computed may be specified by means of a machine learning algorithm, as described below, for optimizing the parameter (for example, parameter2). In one example, a low correlation (for example, a correlation coefficient below or above a specific threshold) between the signals acquired by two sensors arranged at two opposing lateral sides of a head may indicate an increased probability of an injury (for example, a concussion). In one example, a low correlation (for example, a correlation coefficient below or above a specific threshold) between the signals acquired by two sensors, one arranged at the front side and one arranged at the back side of a head may indicate an increased probability of an injury (for example, a concussion).

The relationship between energies given for at least two different frequency ranges of at least one signal of the set of signals may present another parameter (for example parameter3) for determining the indicator. In one example, the relationship is a ratio of energy being determined by comparing a sum or an integral of the energies within a first frequency range to a sum or an integral of energies in a second frequency range. In one example, the first frequency range starts at 0 Hz and ends at x Hz and the second frequency range starts at x Hz and ends at 30 Hz (x may be determined by a machine learning algorithm). The first frequency range may be a frequency range below a lower frequency threshold and may start at frequency zero or for example at more than 10% or 20% of the lower frequency threshold. The second frequency range may be a frequency range above a frequency threshold and may end at the highest determined frequency or for example at 70%, 80% or 90% thereof. For each signal (for example, of each sensor) a respective frequency threshold (lower and/or upper frequency threshold) may be set.

The frequency threshold may be determined by means of a machine learning algorithm, as described below. In one example, for each signal (for example, of each sensor) a respective frequency threshold may be determined by means of a machine learning algorithm, as described below. The relationship between energies given for the two different frequency ranges separated by the frequency threshold may indicate an increased probability for an injury (for example, a concussion).

Parameter1, parameter2 and/or parameter3 may be used for analyzing the acceleration data, average energy data or the heart rate acceleration data, described below. Parameter1, parameter2 and/or parameter3 may be acquired for each signal/each pair of signals acquired by each sensor or each pair of sensors of a plurality of sensors. The results of this analysis may be provided to a machine learning algorithm, as described below.

In one example, the analysis data further describe a rule for combining at least two of:

b1) the determined overall energy level (for example, parameter1), b2) the determined correlation (for example, parameter2), or b3) the determined relationship (for example, parameter3), in order to determine the indicator data based on the combination. Parameter1 and Parameter3 may be determined for one or more selected signals of the set of signals. Parameter2 may be determined for two or more selected signals of the set of signals (for example, for each subset of signals). The selection of the signals for the respective parameters may be optimized by means of a machine learning algorithm, as described below. In one example, the correlation (parameter2) between two signals of two (acceleration) sensors selected from a plurality of signals of various (acceleration) sensors may be combined with the overall energy level (parameter1) and/or the relationship (parameter3) to determine the indicator. Parameter2 for two signals of two selected sensors may be combined with parameter1 and/or parameter3 for the signal of one or more selected sensors of the set of sensors. Combining the parameters and selecting the respective sensors may be performed by means of a machine learning algorithm, as described below.

In one example, the indicator data are determined by means of a machine learning algorithm. The machine learning algorithm may, for example, be a support vector machine, a random forest or a neural network. In one example, the machine learning algorithm uses the analysis data and a plurality of acceleration data (for example, classified acceleration data), the plurality of acceleration data being associated to information on a presence or non-presence of the injury, for performing an optimization of the analysis data. The machine learning may for example use classification and/or regression methods.

In this regard, acceleration data may be acquired for a first population of patients having the injury (for example, clinically diagnosed) and a second population of patients not having the injury (for example, clinically diagnosed). The analysis data used for analyzing this acceleration data are for example used to train the machine learning algorithm and are also referred to as training analysis data. The plurality of training analysis data acquired in such way may be used by the machine learning algorithm to optimize the rules for determining parameter1, parameter2 and/or parameter3, as discussed above. For example, the machine learning algorithm varies at least one of the parameters, for example the thresholds defining the parameters. Values for the optimized parameter1, parameter2 and/or parameter3 may be extracted from any acceleration data (for example, acceleration data acquired for the first and/or second population of patients). The machine learning algorithm may also find an optimal combination of parameter1, parameter2 and/or parameter3 for determining indicator data. The machine learning algorithm may optimize the analysis data. For example the optimization criterion is such that the best reproduction of the clinical diagnosis associated with the training analysis data is achieved.

In one example, the machine learning algorithm may select and combine parameter1, parameter2 and/or parameter3, such that the best possible discrimination power between the first population of patients having the injury and the second population of patients not having the injury is achieved. In other words, the machine learning algorithm may be taught to optimize selection and combination of parameter1, parameter2 and/or parameter3. For example, for determining a (binary) indicator relating to an injury (indicating the presence or non-presence of an injury) the discrimination power may be quantified, for example, by an area under an receiver operating characteristic curve (ROC curve). The ROC curve describes the relation between sensitivity (=true positive rate) and specificity (=true negative rate) of a method or a parameter on a given classification task. For example, for determining an indicator relating to a continuous score for an (potential) injury the discrimination power may be quantified by means of error analysis, for example by means of a sum of squared differences.

After training (teaching) the machine learning algorithm, the method may be applied for newly acquired acceleration data (for example, for a new patient) and the indicator data may be determined with a high accuracy.

In one example, the method comprises executing, on the at least one processor of the at least one computer, a step of determining, based on the acceleration data, average energy data describing an average energy depending on frequency, wherein determining indicator data is based on the average energy data. Accordingly, the frequency spectrum (for example, represented by a waterfall diagram) may be averaged to obtain a periodogram (for example a Welch periodogram). The averaging is for example performed over at least a part of the total time of measurement by using the above-mentioned acceleration data depending on time or for example performed over at least a part of the range of heart rates by using heart rate acceleration data depending on heart rate (see below).

In one example, the method comprises executing, on the at least one processor of the at least one computer, the steps of:

acquiring heart rate data describing a heart rate of the patient (as a function of time), determining, based on the heart rate data and the acceleration data, heart rate acceleration data describing the energy of the signal in dependence on frequency for different heart rates, by sorting frequency contents of the signal according to the heart rate, the frequency contents describing the energy in dependence on frequency for different times, wherein determining the indicator data is based on the heart rate acceleration data by applying the analysis rule to the heart rate acceleration data. Accordingly, the acceleration data may be associated to the heart rate. As mentioned above, the heartbeat may function as a test beat for analyzing the resonance behavior of at least part of the brain.

In one example, the basis for determining (for example, defining or setting) parameter1, parameter2 and/or parameter3 may be acceleration data, average energy data or heart rate acceleration data, as described above. In one example, optimizing parameter1, parameter2 and/or parameter3 by means of a machine learning algorithm (for example by determining thresholds defining the parameters) may be based on acceleration data, average energy data or heart rate acceleration data, as described above.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect and/or to a (physical, for example electrical, for example technically generated) signal wave, for example a digital signal wave, carrying information which represents the program, for example the aforementioned program, which for example comprises code means which are adapted to perform any or all of the method steps described herein.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the at least one processor or is loaded into the at least one memory, or wherein the at least one computer comprises the program storage medium according to the third aspect.

In a fifth aspect, the invention is directed to a system configured to determine an indicator relating to an injury of an anatomical structure of a patient, the system comprising:

a) at least one sensor; and b) the at least one computer according to the fourth aspect; wherein the at least one computer is operatively associated with the at least one sensor. For example, the computer receives measurement signals from the at least one sensor which measurement signals represent the acceleration data.

It is within the scope of the present invention to combine one or more features of one or more embodiments or aspects of the invention in order to form a new embodiment wherever this is technically expedient and/or feasible.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

In particular, the invention does not involve or in particular comprise or encompass an invasive step which would represent a substantial physical interference with the body requiring professional medical expertise to be carried out and entailing a substantial health risk even when carried out with the required professional care and expertise. More particularly, the invention does not involve or in particular comprise or encompass any surgical, therapeutic or diagnostic activity. The invention is instead directed to medical data processing method for determining an indicator relating to an injury of an anatomical structure of a patient. No physician is involved in carrying out the method. No surgical, therapeutic or diagnostic activity and in particular no surgical, therapeutic, or diagnostic step is necessitated or implied by carrying out the invention.

DESCRIPTION OF THE FIGURES

In the following, the invention is described with reference to the appended figures which represent a specific embodiment of the invention. The scope of the invention is however not limited to the specific features disclosed in the context of the figures, wherein FIG. 1a shows a frontal view of an exemplary system for performing the disclosed method;

FIG. 1b shows a lateral view of the system performing the disclosed method;

As shown in FIGS. 1a and 1b, an exemplary system performing the disclosed method comprises, for example, six acceleration sensors 2 attached to the surface of an anatomical structure embodied by a patient's head 1. The acceleration sensors 2 are configured to measure vibrations, which are triggered, for example by the heartbeat of the patient, on the surface of the head 1 and to transmit corresponding signals via data transmission connections 4 (such as a wireless connection or cables) to a computer 3.

FIG. 2 shows a schematic view of the exemplary system for performing the disclosed method. The computer 3 is operably coupled to the plurality of acceleration sensors 2. The computer 3 comprises a processor 5, a memory 6 and an interface 7. The computer 3 is connected to an input unit 8, such as a mouse, a keyboard or a touch-sensitive surface, and an output unit 9 such as a display, a speaker or a tactile sensation generation unit. A program causing the computer 3 to perform the disclosed method may be loaded into the memory 6 of the computer. In one embodiment the program may be stored on a program storage medium comprised in or connected to the computer 3.

FIG. 3 is a flow diagram illustrating the basic steps of the disclosed method, which in the illustrative example of FIG. 3 starts with a step S1 of acquiring acceleration data. Then, step S2 is executed which encompasses acquiring analysis data. In subsequent step S3 indicator data is determined based on the acceleration data and the analysis data.

In one example, step S1 of acquiring acceleration data comprises measuring the acceleration of the anatomical structure by each acceleration sensor 2 for a certain recording period (for example, one or more minutes). Accordingly, each acceleration sensor 2 measures a time-dependent voltage signal. The time-dependent signal of each acceleration sensor 2 is converted to the frequency domain, for example by means of an overlapping Fast Fourier Transform (FFT).

Accordingly, a frequency spectrum is acquired for the signal of each acceleration sensor 2.

Figure 2:
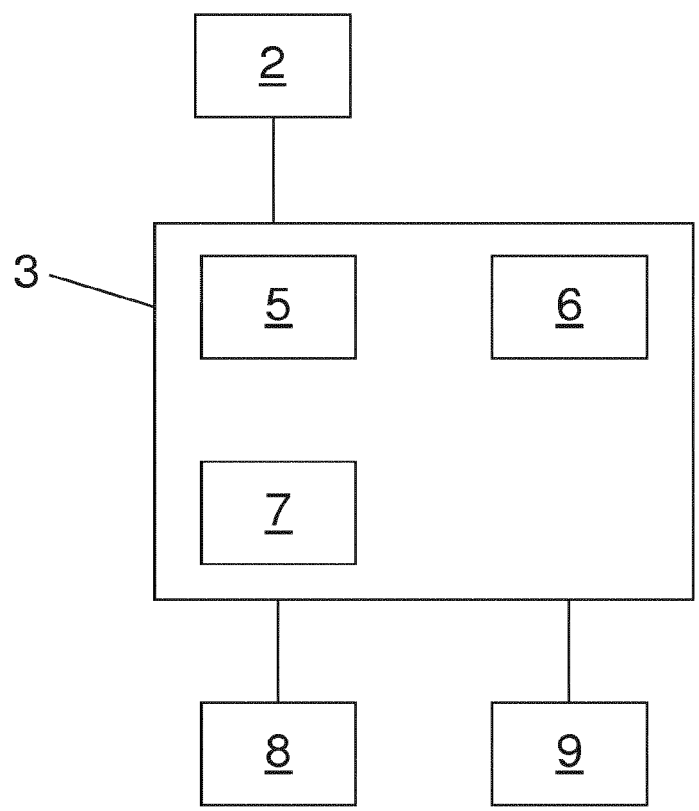
FIG. 2 shows a schematic view of the system performing the disclosed method.
Figure 3:
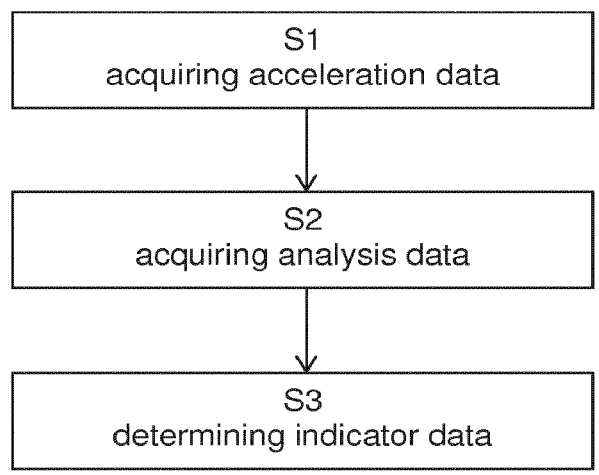
FIG. 3 is a flow diagram showing the basic steps of the disclosed method.
Figure 4:
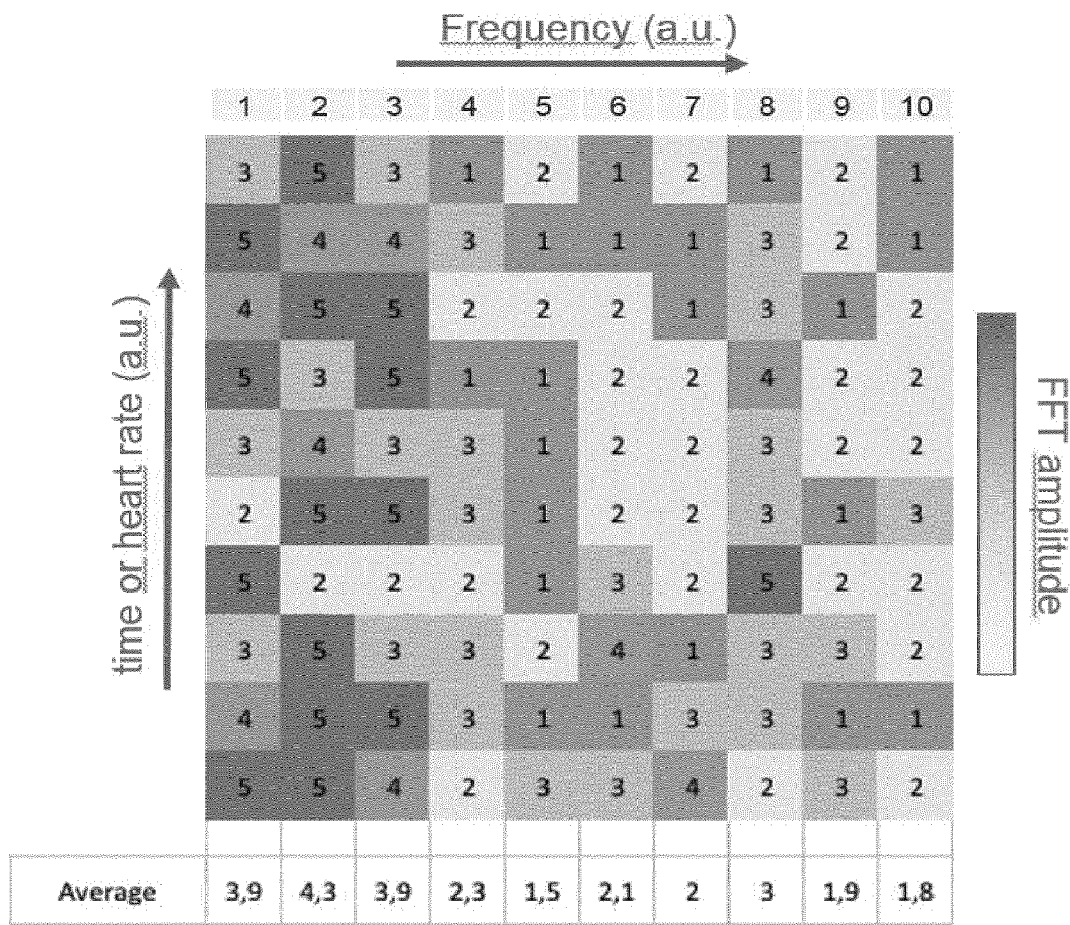
FIG. 4 is a waterfall diagram of a frequency spectrum for the signal measured by one acceleration sensor.

The frequency spectrum may be depicted in a waterfall diagram, as shown in FIG. 4. The energy (FFT amplitude) of the signal may be depicted as a function of time, i.e. the time intervals (for example, each interval being one or more seconds) are sorted chronologically along the y-axis. Alternatively, the time intervals may be sorted according to the heart rate of the patient (described by acquired heart rate data) along the y-axis.

Figure 5:
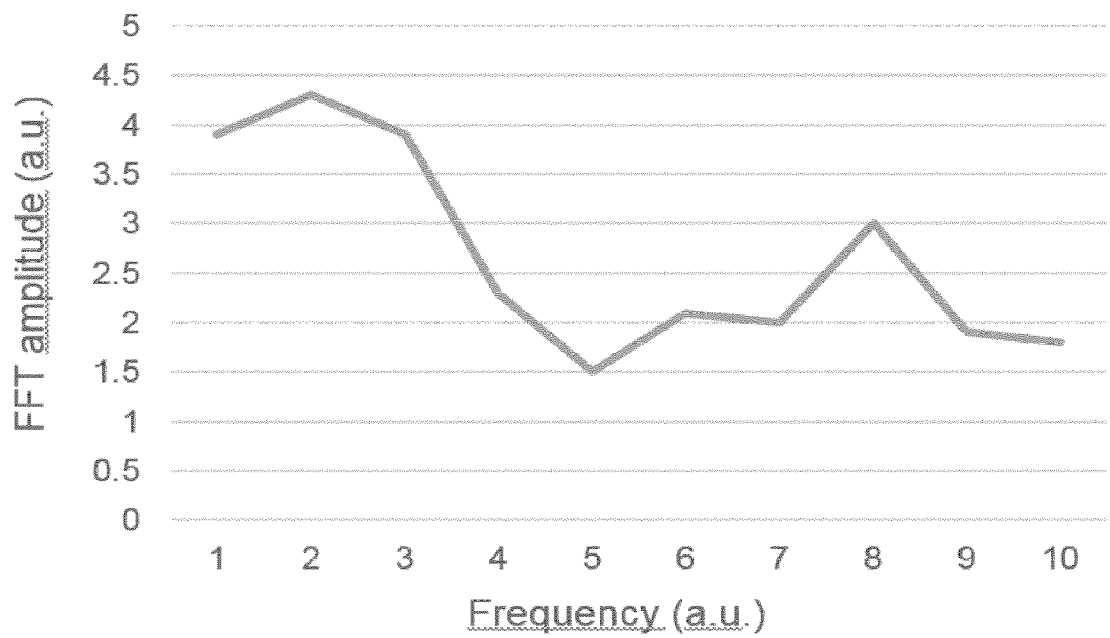
FIG. 5 is a periodogram obtained by averaging the waterfall diagram of FIG. 4 along the y-axis.

In one example, average energy data describing an average energy depending on frequency is determined for each acceleration sensor 2. The average energies may be depicted in a periodogram, as shown in FIG. 5. The periodogram of FIG. 5 is obtained by averaging values of the waterfall diagram of FIG. 4 along the y-axis. The waterfall diagram of FIG. 4 represents acceleration data or heart rate acceleration data, as described above. The periodogram of FIG. 5 represents average energy data, as described above.

The invention claimed is:

1. A medical method for determining an indicator relating to an injury of an anatomical structure of a patient, the method comprising executing, on at least one processor of at least one computer, the steps of:
   acquiring acceleration data describing an energy of a set of one or more signals in dependence on both time and frequency, the set of signals acquired by measuring the acceleration of the anatomical structure over time;
   acquiring analysis data describing an analysis rule for determining a correlation between at least two signals of the set of signals, the at least two signals respectively measured at least two different respective regions of the anatomical structure;
   determining indicator data describing the indicator based on the acceleration data and the analysis data; and
   wherein the correlation is determined by computing a correlation coefficient describing a correlation between a first signal of the set of signals acquired at a first region of the anatomical structure and a second signal of the set of signals acquired at a second region of the anatomical structure.

2. The method according to preceding claim 1, wherein the indicator data are determined by a machine learning algorithm.

3. The method according to claim 2, wherein the machine learning algorithm uses the analysis data, a plurality of acceleration data or combinations thereof, the plurality of acceleration data being associated to information on a presence or non-presence of the injury, for performing an optimization of the analysis data.

4. The method according to claim 1, further comprising executing, on the at least one processor of the at least one computer, a step of:
   determining, based on the acceleration data, average energy data describing an average energy depending on frequency; and
wherein determining indicator data is based on the average energy data.

5. The method according to claim 1, further comprising executing, on the at least one processor of the at least one computer, the steps of:
   acquiring heart rate data describing a heart rate of the patient;
   determining, based on the heart rate data and the acceleration data, heart rate acceleration data describing the energy of the signal in dependence on frequency for different heart rates, by sorting frequency contents of the signal according to the heart rate, the frequency contents describing the energy in dependence on frequency for different times; and
   wherein determining the indicator data is based on the heart rate acceleration data by applying the analysis rule to the heart rate acceleration data.

6. The method according to claim 1, further comprising executing, on the at least one processor of the at least one computer, the step of:
   acquiring threshold data describing a threshold for the energy; and
   wherein the overall energy level is determined by comparing the threshold with the energy.

7. The method according to claim 1, wherein the acceleration data is acquired by at least two sensors respectively arranged at different regions of the anatomical structure or respectively receiving signals from different regions of the anatomical structure.

8. The method according to claim 1, wherein the set of signals are acquired by analyzing a time dependent acceleration signal with respect to time and frequency by means of a joint time frequency analysis (JFTA) by applying a Fourier transformation to the acceleration signal for a plurality of time intervals.

9. A non-transitory computer-readable program storage medium comprising instructions causing at least one processor to:
   acquire acceleration data describing an energy of a set of one or more signals in dependence on both time and frequency, the set of signals acquired by measuring the acceleration of an anatomical structure over time;
   acquire analysis data describing an analysis rule for determining a correlation between at least two signals of the set of signals, the at least two signals respectively measured at least two different respective regions of the anatomical structure;
   determine indicator data describing the indicator based on the acceleration data and the analysis data; and
   wherein the correlation is determined by computing a correlation coefficient describing a correlation between a first signal of the set of signals acquired at a first region of the anatomical structure and a second signal of the set of signals acquired at a second region of the anatomical structure.

10. A system to determine an indicator relating to an injury of an anatomical structure of a patient, comprising:
   at least one sensor; and
   the at least one computer having at least one processor and associated memory, the memory having instructions stored thereon to:
   acquire acceleration data describing an energy of a set of one or more signals in dependence on both time and frequency, the set of signals acquired by measuring the acceleration of the anatomical structure over time;
   acquire analysis data describing an analysis rule for determining a correlation between at least two signals of the set of signals, the at least two signals respectively measured at least two different respective regions of the anatomical structure;
   determine indicator data describing the indicator based on the acceleration data and the analysis data;
   wherein the correlation is determined by computing a correlation coefficient describing a correlation between a first signal of the set of signals acquired at a first region of the anatomical structure and a second signal of the set of signals acquired at a second region of the anatomical structure; and wherein the at least one computer is operatively associated with the at least one sensor.

\* \* \* \* \*